(12) United States Patent
Antinozzi

(10) Patent No.: US 8,404,179 B2
(45) Date of Patent: Mar. 26, 2013

(54) SPORTS EQUIPMENT SANITIZER

(75) Inventor: Michael Antinozzi, Windsor (CA)

(73) Assignee: Ozone Nation Inc., Windsor, Ontario (CA)

( * ) Notice: Subject to any disclaimer, the term of this patent is extended or adjusted under 35 U.S.C. 154(b) by 0 days.

(21) Appl. No.: 13/304,867

(22) Filed: Nov. 28, 2011

(65) Prior Publication Data

US 2012/0070337 A1 Mar. 22, 2012

Related U.S. Application Data

(62) Division of application No. 11/582,686, filed on Oct. 18, 2006.

(30) Foreign Application Priority Data

Oct. 19, 2005 (CA) ...................................... 2526367

(51) Int. Cl.
*A61L 9/00* (2006.01)
(52) U.S. Cl. ........................................... 422/5; 422/292
(58) Field of Classification Search .................. 422/292, 422/5; 34/103, 104
See application file for complete search history.

(56) References Cited

U.S. PATENT DOCUMENTS

| | | | |
|---|---|---|---|
| 3,513,564 A | 5/1970 | Gramprie | |
| 3,645,009 A | 2/1972 | Ketchum | |
| 3,793,744 A | 2/1974 | Saita | |
| 4,145,602 A | 3/1979 | Lee | |
| 4,178,092 A | 12/1979 | Yamamoto et al. | |
| 4,625,432 A | 12/1986 | Baltes | |
| 4,853,735 A | 8/1989 | Kodama et al. | |
| 5,087,943 A | 2/1992 | Creveling | |
| 5,120,512 A | 6/1992 | Masuda | |
| 5,371,577 A | 12/1994 | Fujimura et al. | |
| 5,528,840 A | 6/1996 | Pajak et al. | |
| 5,592,750 A | 1/1997 | Eichten | |
| 6,090,188 A | 7/2000 | Yang et al. | |
| 6,134,806 A | 10/2000 | Dhaemers | |
| 6,327,792 B1 | 12/2001 | Hebert | |
| 6,577,828 B1 | 6/2003 | Ramos | |
| 6,598,431 B2 | 7/2003 | Teran et al. | |
| 6,845,569 B1 | 1/2005 | Kim | |
| 6,889,449 B2 | 5/2005 | Silver | |
| 7,103,989 B2 | 9/2006 | Rosseau et al. | |
| 2005/0193585 A1 | 9/2005 | Silver | |
| 2005/0204579 A1* | 9/2005 | Rosseau et al. | ................. 34/104 |
| 2006/0037899 A1 | 2/2006 | Liou | |

* cited by examiner

*Primary Examiner* — Kevin Joyner
(74) *Attorney, Agent, or Firm* — Carlson, Gaskey & Olds, P.C.

(57) ABSTRACT

An apparatus for removing mold and mildew from sports equipment includes an ozone generator that supplies ozone to a distribution system that directs ozone at a high velocity to both dry and sanitize sports equipment. The high velocity flow of ozone is directed to the interior portions of the sports equipment to dry and sanitize the equipment. The high speed flow of the ozone provides for drying of the interior surfaces of the equipment while also direction impinging ozone flow on interior surfaces to remove undesirable mold and mildew.

8 Claims, 3 Drawing Sheets

SPORTS EQUIPMENT SANITIZER

CROSS REFERENCE TO RELATED APPLICATION

This application is a divisional application of U.S. patent application Ser. No. 11/582,686 filed Oct. 18, 2006, which claims priority to Canadian Patent Application No. 2,526,367 filed Oct. 19, 2005.

BACKGROUND OF THE INVENTION

This invention generally relates to sanitizing, and deodorizing sports equipment. More particularly, this invention relates to a method and device for safely sanitizing and deodorizing sports equipment utilizing ozone.

Sports equipment that is used frequently grows mold and mildew that in turn create an undesirable odor. Sprays available to consumers mask such odors, but only for a short period and do not remove the mold and mildew that cause the odors and that can cause a variety of serious health issues.

There are machines on the market, as shown for example in Canadian Patent 2385170, that surround the equipment in ozone. Machines of this type are, however, inefficient because the ozone does not fully penetrate the equipment. The effectiveness of such devices is further reduced when the equipment is wet or damp, as the desirable sanitizing properties of ozone are reduced by the presence of moisture.

SUMMARY OF THE INVENTION

An example apparatus for removing mold and mildew from sports equipment includes an ozone generator that supplies ozone to a distribution system that directs ozone at a high velocity to both dry and sanitize sports equipment.

The example apparatus includes an ozone generator that produces ozone that is fed into various sport equipment support conduits. The conduits include perforated sections that fit within the various sports equipment. The ozone is drawn through the conduits by fans that push ozone at high velocity out the perforated sections to penetrate the interior of the sports equipment. The high velocity flow of ozone is directed to the interior portions of the sports equipment to dry and sanitize the equipment. The high speed flow of the ozone provides for drying of the interior surfaces of the equipment while also directing impinging ozone flows to remove undesirable mold and mildew.

These and other features of the present invention can be best understood from the following specification and drawings, the following of which is a brief description.

DETAILED DESCRIPTION OF THE PREFERRED EMBODIMENT

Figure 1:
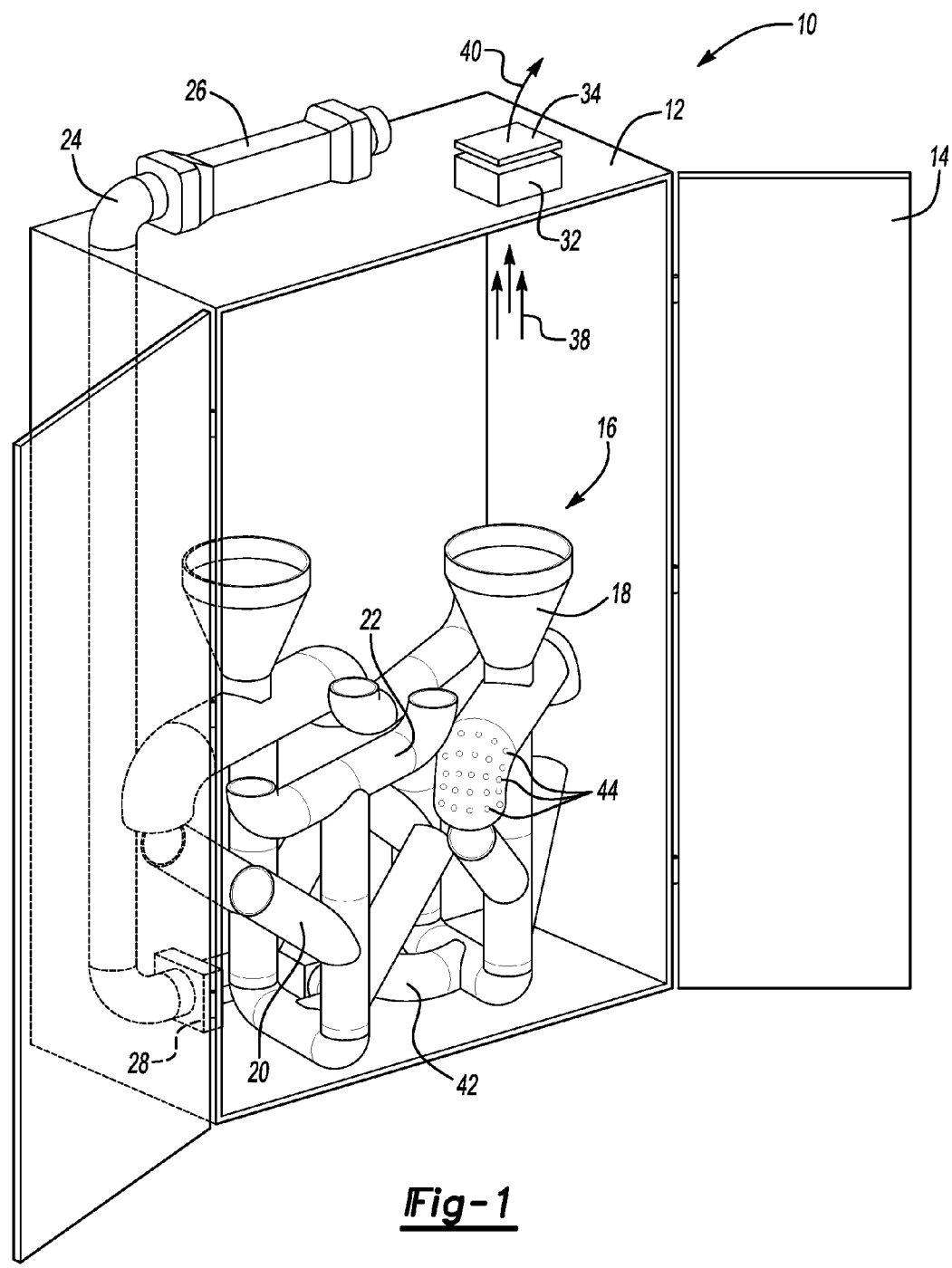
FIG. 1 is a perspective view of an example sports equipment sanitizing device.
Figure 2:
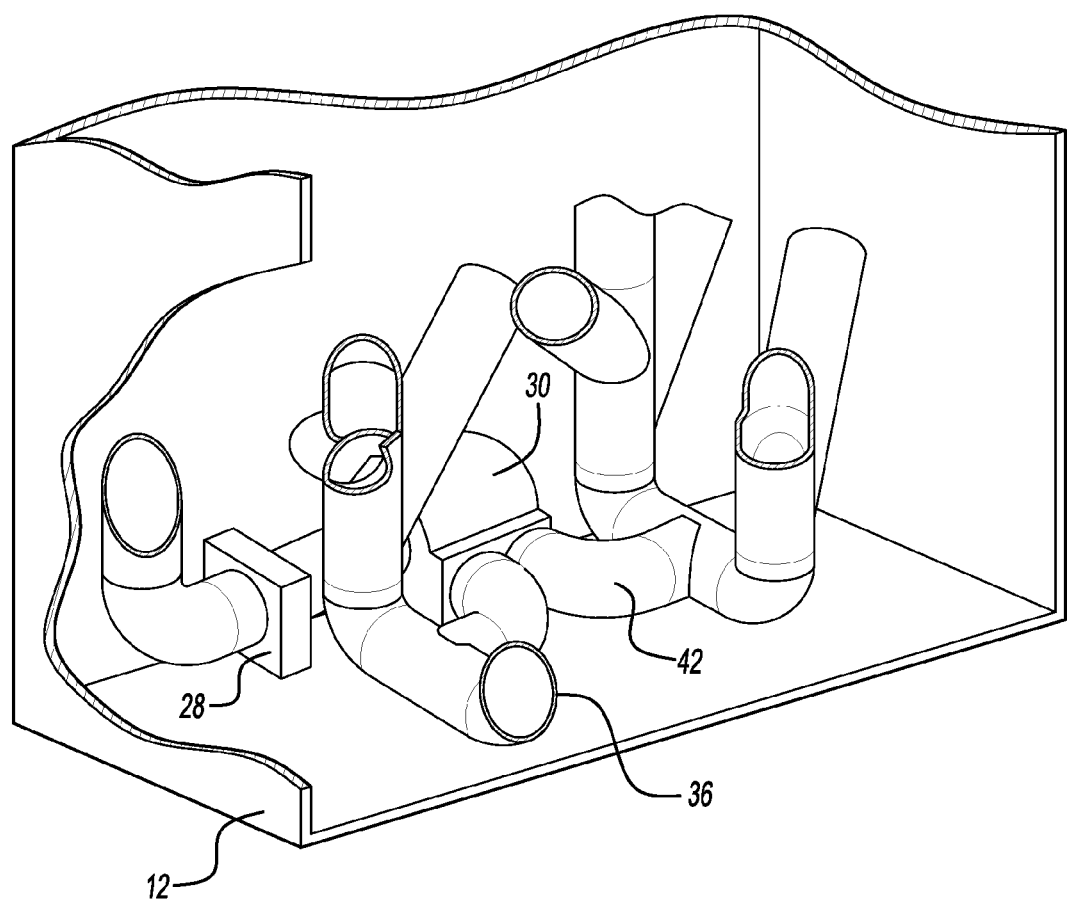
FIG. 2 is a perspective view of a portion of the example sports equipment sanitizing device.

Referring to FIGS. 1 and 2, a sports equipment sanitizing assembly 10 includes a distribution system 16 mounted within a sealable cabinet 12. The cabinet 12 includes doors 14 for enclosing and sealing the interior of the cabinet 12. The distribution system 16 includes a plurality of conduits for supporting various sports equipment for deodorizing and sanitizing.

The conduits of the distribution system 16 receive and inject a flow of ozone enriched air into the sports equipment to remove odor and sanitize the item. The conduits are configured into various forms to hold the various sports equipment, such as skates, gloves, shoulder pads, etc. The distribution system 16 includes a plurality of openings disposed to direct the ozone enriched air into an interior space of the equipment item. The interior space is the location of the source of odor and therefore merely surrounding an item with ozone is not effective in removing and sanitizing the equipment.

An ozone generator 26 is supported on the cabinet 12 and supplies ozone through conduit 24. Ozone from the generator 26 is drawn into the distribution system 16, first by a low volume fan 28. The low volume fan 28 draws the ozone from the ozone generator 26 into a plenum 42. Various conduits that vary in shape to accept different sports equipment are in communication with the plenum 42. A high speed fan 30 is disposed adjacent or within the plenum to increase the flow rate of ozone enriched air through the distribution system 16. The increased velocity of air flow through the distribution system pushes ozone enriched air out a plurality of openings 44.

Ozone enriched air exiting the plurality of openings 44 is injected against an interior surface of the sports equipment mounted thereon. The sports equipment is supported on the distribution system portion but is not sealed, thereby allowing flow of air out of the particular item and into the enclosed cabinet. The air that flows from the item is ozone rich and is drawn into an ozone destruction device 32. Ozone is potentially toxic to humans and therefore must be flushed from the cabinet prior to unsealing the cabinet. The Ozone concentration within the cabinet 12 is reduced to desired levels by the destruction device 32 and the vent 40. The destruction device 32 includes a chemical compound, such as for example manganese dioxide, that is known to deconstruct ozone and provide for a quick venting of the cabinet to reduce the overall time required to deodorize and sanitize equipment. Although, the example destruction device 32 utilized manganese dioxide as the destruction compound, other materials know to those skilled in the art for deconstructing ozone are within the contemplation of this invention.

A spray unit 36 is in communication with the plenum 42, and thereby the entire distribution system 16. The spray unit 36 introduces a liquid deodorant into the distribution system that is vaporized and blown into the various items to complete the deodorizing and sanitizing process. The spray unit 36 is utilized to inject compounds in liquid form that provide a desired smell and that inhibits the reformation of molds and mildew within the various sports equipment items.

Figure 3:
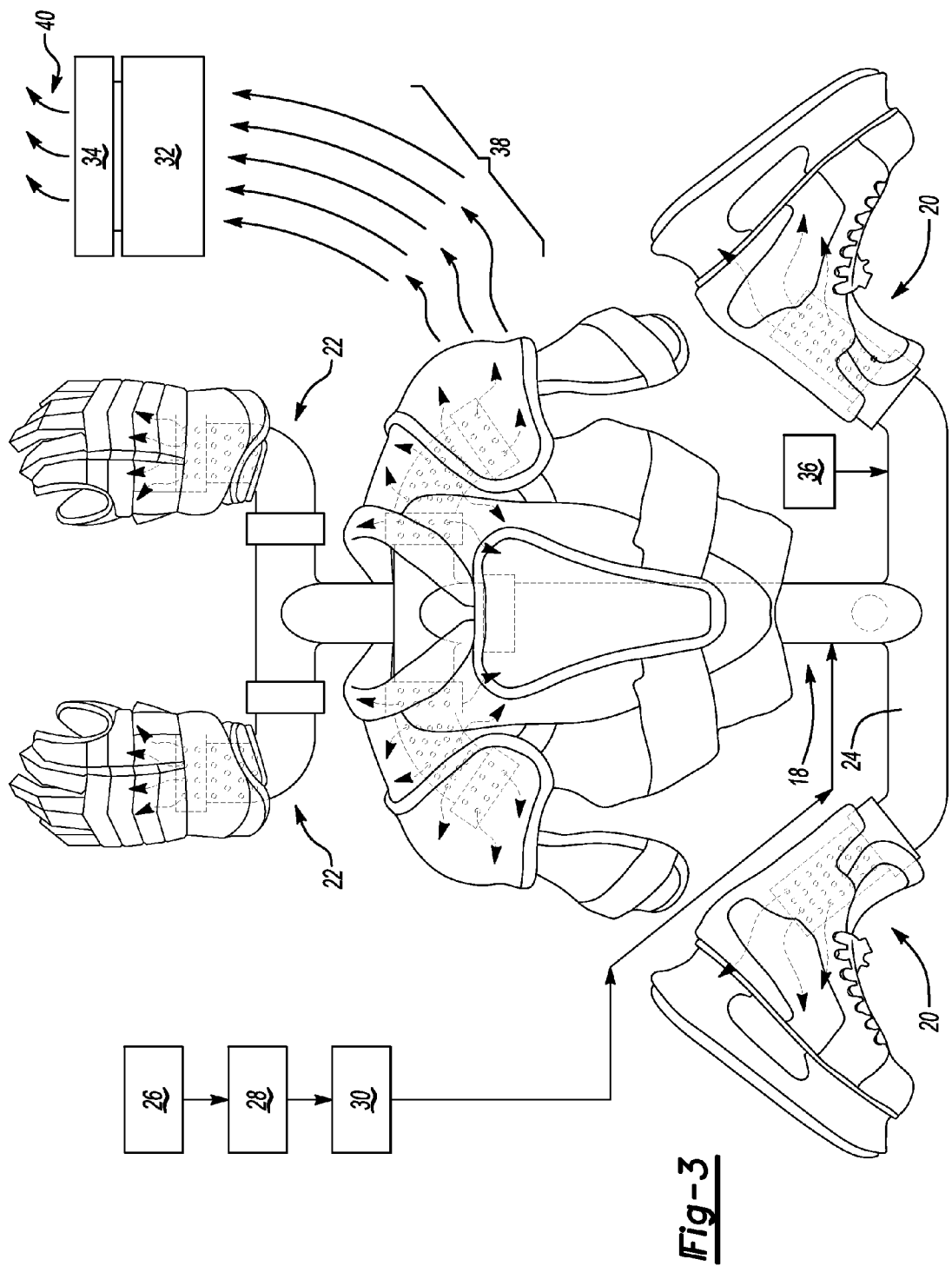
FIG. 3 is a schematic view of an example distribution system for the example sanitizing device.

Referring to FIG. 3, the example distribution system 12 includes various portions for supporting different types of sports equipment. The distribution system 12 includes the torso portion 18 that replicates a human torso. The torso portion 18 supports items such as chest protectors, and shoulder pads such that a plurality of openings can direct ozone rich air against an interior surface. The distribution system also includes a glove portion 22 for supporting gloves. A plurality of opening are disposed to direct ozone rich air against the interior surface of each of the gloves. The distribution system further includes a foot portion 20 for supporting items such as skates, boots or shoes. As with the other portions of the distribution system 12, the foot portion 20 includes a plurality of openings for directing ozone rich air against the inner surfaces of the skate, shoe or boot.

The specific direction of ozone to impinge on the inner surfaces of the particular sports items increases the efficiency and effectiveness of the ozone rich air. Further, as the ozone rich air is directed to the specific locations that require sanitization, less ozone is required, for a reduced time.

Referring again to FIGS. 1 and 2, the sanitizing assembly 10 operates by first mounting the various sports items onto corresponding specifically orientated portions of the distribution system 12. As appreciated, the example distribution system is orientated for deodorizing and sanitizing hockey equipment such as gloves, skates and chest protector, however, other orientations of the distribution system can be configured to support equipment specific to other sports.

Once the equipment is mounted on the distribution system 12, the cabinet 12 is closed and sealed. The ozone generator 26 is then actuated to begin producing ozone. Concurrently, the low speed fan 28 is turned on to being drawing ozone rich air into the plenum 42. As ozone rich air builds in the plenum, the high speed fan 30 is actuated to begin pushing the ozone rich air through the distribution system 12 and out the plurality of openings 44. The high speed fan 30 operates to provide airflow sufficient to penetrate the various sports items. The high velocity of ozone rich air provides for drying the interior surfaces of the equipment in a quick manner to improve the effectiveness of the ozone. Ozone works most effectively on dry surfaces. Therefore, the high speed air is utilized to produce a dry surface conducive to the effective operation of the ozone on the mold and mildew that cause the undesirable odor.

The cycle time that the high speed fan 30 and ozone generator 26 are on varies relative to the specific equipment and amount of mold and mildew present. The cycle time can be adjusted to affect the desired sanitation based on the size and other factors of the sports equipment.

Once the sanitization of the equipment is complete, the ozone generator 26 is switched off to stop the creation of ozone. However, ozone remains in the cabinet 12. Merely venting the ozone from the cabinet is not always desirable depending on the location of the assembly. The ozone is therefore first drawn through the deconstructing device 32. The deconstructing device 32 includes a compound, in this example manganese dioxide, that reacts with or encourages reactions that transform the ozone into harmless elements such as oxygen. The transformed air is then vented from the cabinet to reduce the ozone level with the cabinet 12 to a desired level. The cabinet 12 then can be opened and the equipment removed.

Accordingly, the distribution system directs ozone rich air against the interior surface of the sports equipment to dry, deodorize, and sanitize the item. Further, the assembly 10 includes an ozone destruction device to quickly reduce the concentration of ozone within the cabinet once the sanitization process is complete.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. A method of sanitizing and deodorizing sports equipment comprising the steps of:
   mounting an item to a portion of ductwork including a plurality of perforations;
   enclosing the item and ductwork within a sealable cabinet such that the environment within the sealable cabinet is completely contained without any openings communicate air to an environment exterior to the sealable cabinet;
   generating ozone;
   drawing the generated ozone into the ductwork and out the plurality of perforations;
   spraying an anti-bacterial fluid into the ductwork for release through the plurality of perforations;
   reacting the ozone with a chemical compound to facilitate transformation of ozone into non-harmful elements before communicating an internal space within the sealable cabinet with the environment exterior to the sealable cabinet; and
   exhausting the non-harmful elements from the sealable cabinet.

2. The method as recited in claim 1, including the step of deconstructing the ozone released from the ductwork.

3. The method as recited in claim 1, wherein the step of exhausting non-harmful elements from the sealable cabinet occurs only after the step of reacting the ozone to transform the ozone into the non-harmful elements and until the environment within the cabinet contains a desired level of ozone.

4. The method as recited in claim 1, wherein the step of generating ozone comprises generating a desired level of ozone determined to sanitize for distribution through the ductwork and out the plurality of perforations.

5. The method as recited in claim 1, wherein said step of drawing ozone through the ductwork comprise drawing the ozone rich air through the ductwork at a flow rate determined to penetrate the sports equipment.

6. The method as recited in claim 1, wherein the ductwork includes a portion simulating a human torso for supporting an item worn on a human torso.

7. The method as recited in claim 1, wherein the ductwork includes a portion simulating a human hand for supporting an item worn on a human hand.

8. The method as recited in claim 1, wherein the chemical compound comprises manganese dioxide.

\* \* \* \* \*